US00PP11275P

United States Patent [19]

Keeter et al.

[11] Patent Number: Plant 11,275

[45] Date of Patent: Mar. 7, 2000

[54] VERBENA PLANT NAMED 'COLKEETER'

[75] Inventors: Thomas Keeter, San Antonio; Agnes Hubbard, Fair Oaks Ranch; James Spivey, Devine, all of Tex.

[73] Assignee: Color Spot Nurseries, Inc., Pleasant Hill, Calif.

[21] Appl. No.: 08/940,111

[22] Filed: Sep. 29, 1997

[51] Int. Cl.[7] ..... A01H 5/00

[52] U.S. Cl. ..... Plt./308

[58] Field of Search ..... Plt./87, 308

[56] References Cited

PUBLICATIONS

Hortus Third: A Concise Dictionary of Plants Cultivated in the United States and Canada. Bailey et al. pp. 1208–1225, 1976.

*Primary Examiner*—Howard J. Locker
*Assistant Examiner*—Anne Marie Grünberg
*Attorney, Agent, or Firm*—C. A. Whealy

[57] ABSTRACT

A distinct cultivar of Verbena plant named 'Colkeeter', characterized by its upright, outwardly spreading and freely branching plant habit; numerous inflorescences of bright red flowers with intense purple star at center; vigorous growth habit; small dark green leaves; and high temperature, high light and frost tolerance.

2 Drawing Sheets

The present invention relates to a new and distinct cultivar of Verbena plant, botanically known as *Verbena* × *hybrida,* and hereinafter referred to by the cultivar name Colkeeter. The new cultivar was discovered and selected by the inventors in 1995 from seedling progeny from a cross of unidentified selections of *Verbena* × *hybrida* in a garden in San Antonio, Tex. Asexual reproduction of the new cultivar by cuttings taken in San Antonio, Tex., has shown that the unique features of this new Verbena are stable and are reproduced true to type in successive propagations. The cultivar Colkeeter has not been observed under all possible environmental conditions. The phenotype may vary somewhat with variations in environment such as temperature, light intensity, and fertility level, without, however, any variance in genotype. The following traits have been repeatedly observed and are determined to be the unique characteristics of 'Colkeeter'. These characteristics in combination distinguish 'Colkeeter' as a new and distinct cultivar:

1. Upright, outwardly spreading and freely branching plant habit.
2. Numerous inflorescences of bright red flowers with intense purple star at center.
3. Vigorous growth habit.
4. Small dark green leaves.
5. High temperature, high light and frost tolerant. Plants of the new Verbena can be compared to the *Verbena* × *hybrida* cultivar Sarah's Pink (not patented). However in side-by-side comparisons conducted in San Antonio, Tex., plants of the new Verbena were more spreading, had smaller and more dissected foliage, and flower color was darker and more iridescent. Plants of the new Verbena can also be compared to the *Verbena* × *hybrida* cultivar Fiesta (not patented). However in side-by-side comparisons conducted in San Antonio, Tex., plants of the new Verbena were more vigorous, floriferous and heat tolerant. In addition, plants of the new Verbena differed in flower color and were self-cleaning whereas plants of the cultivar Fiesta had persistent (not self-cleaning) flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical plant of the cultivar Colkeeter planted in a landscape setting.

The upper photograph on the second sheet comprises a close-up view of typical flowers of the cultivar Colkeeter.

The lower photograph on the second sheet comprises a close-up view of the lower surface of typical flowers. Flower and foliage colors in the photographs may appear different than the actual colors due to light reflectance.

DETAILED BOTANICAL DESCRIPTION

The following observations and measurements describe plants grown during the spring and summer in San Antonio and Keller, Tex. under full sun. Day temperatures ranged from 10 to 38° C. and night temperatures ranged from 4 to 27° C. In the following description, color references are made to The Royal Horticultural Society Colour Chart except where general terms of ordinary dictionary significance are used.

Botanical Classification: *Verbena* × *hybrida* cultivar Colkeeter.

*Male, or pollen parent.*—Unidentified selection of *Verbena* × *hybrida*.

*Female, or seed parent.*—Unidentified selection of *Verbena* × *hybrida*.

Propagation:

*Type cutting.*—Cuttings.

*Time to initiate roots.*—Summer: About 15 days at temperatures of 27 to 35° C. Winter: About 20 days at temperatures of 16 to 21° C.

*Time to develop roots.*—Summer: About 20 to 25 days at temperatures of 21 to 35° C. Winter: About 42 days at temperatures of 22° C.

*Rooting habit.*—Vigorous, numerous, fine, and freely branching.

Plant Description:

*Form.*—Upright and outwardly spreading perennial shrub.

*Production time.*—From a rooted cutting, usually 5 to 9 weeks are required to produce a finished one-gallon container. Production time will depend on actual environmental conditions and cultural treatments employed.

*Branching habit.*—Freely branching, lateral branches form at every node. Plants are full, dense and bushy. Removal of the terminal apex (pinching) stimulates development of lateral branches.

*Plant height.*—About 30 cm.

*Plant width.*—About 60 cm. Vigor: Vigorous.

*Lateral stem description.*—Internode length: About 3.5 cm. Diameter: About 2 mm. Texture: Very fine pubescence. Color: Greener than 147B.

*Foliage description.*—Leaves single, opposite, generally symmetrical, durable, and long-persisting. Length: About 2.5 cm. Width: About 2 cm. Shape: Roughly ovate. Apex: Acute. Base: Cuneate. Margin: Dissected. Texture: Pubescent on both surfaces, leathery. Durability: Very tolerant to high temperature and drought stresses. Color: Young leaves, upper surface: Darker than 147A. Young leaves, lower surface: Greener than 147B. Mature leaves, upper surface: Darker than 147A. Mature leaves, lower surface: Greener than 147B. Venation, upper surface: 147A/147B. Venation, lower surface: 147C. Petiole: Length: About 6 mm. Diameter: About 1.75 mm. Color: 147B/147C.

Flower Description:

*Flower type and habit.*—Single star-shaped flowers with 5-parted corolla. Calyx five-parted. Flowers arranged in terminal or axillary corymbs. Flowers flat and face upward. Freely flowering, numerous flowers open simultaneously. Usually 10 to 20 flowers per terminal corymb. Flowers self-cleaning.

*Natural flowering season.*—Spring through fall. Plants will continue to flower under conditions of high heat and frost.

*Fragrance.*—None.

*Corymbs length.*—About 4 cm.

*Corymb diameter.*—About 4.5 cm.

*Flower diameter.*—About 1.75 cm by 1.6 cm.

*Flower depth* (*height*).—About 1.5 cm.

*Petals.*—Appearance: Smooth, satiny. Quantity: Five fused at base. Length: From center, about 7.5 mm. Width: About 7.5 mm. Aspect: Flat. Shape: Lobed. Apex: Emarginate. Margin: Entire. Color: Initially bright red, then intense purple eye and star develop. With further development, petals become pinkish red with fainter purple star. When opening, upper surface: 45B with purple, 57A, star. Two purple, 57A, longitudinal streaks on each petal. When opening, lower surface: 45C/45D fading to white at base, faint purple, close to 61C, streaks. Fully opened, upper surface: 45B with purple, close to 66A, star. Flower color fades to 45C/45D and star becomes fainter purple, close to 61C, with development. Fully opened, lower surface: 45C at margins, fading to white at base. Throat: White, whiskered. Tube: White, 155D, to very light green.

*Calyx.*—Shape: Cylinder of five sepals fused at base. Length: About 1 cm. Diameter: About 2 mm. Sepal shape: Linear, narrow, fused until apex. Sepal apex: Acute. Sepal margin: Entire. Sepal texture: Pubescent. Color, both surfaces: Greener than 146A.

*Reproductive organs.*—Androecium: Stamen number: Four. Anther shape: Bi-lobate. Anther size: Less than 1 mm. Anther color: Lemon yellow, 1A. Amount of pollen: Moderate. Pollen color: Lemon yellow, 1A. Gynoecium: Pistil length: About 1.35 cm. Style color: Green, lighter at base. Stigma color: Green.

Disease resistance: The new Verbena has not been observed to be resistant, tolerant or susceptible to pathogens common to Verbena.

Seed production: Seed production has not been observed.

It is claimed:

1. A new and distinct cultivar of Verbena plant named 'Colkeeter', as illustrated and described.

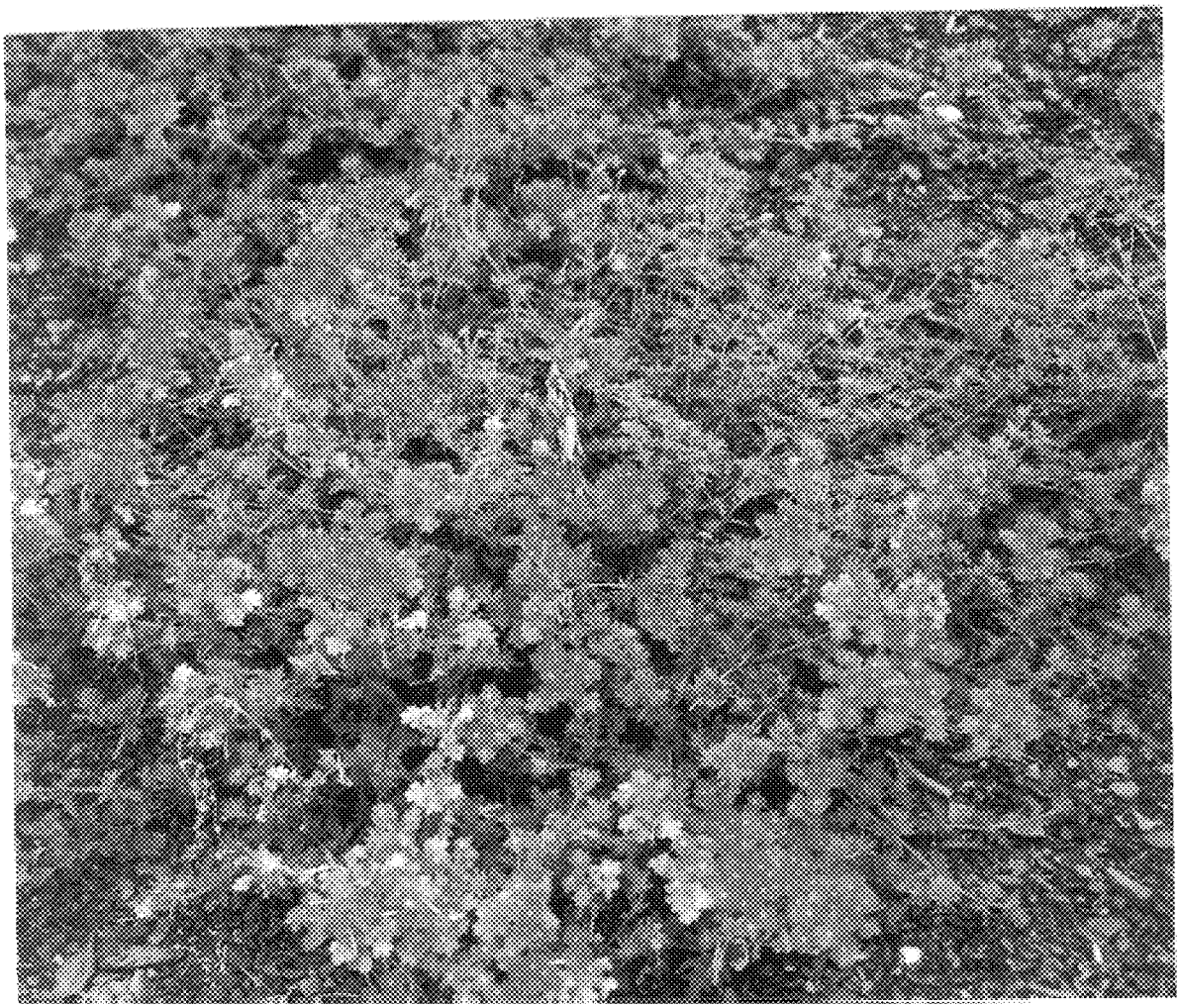

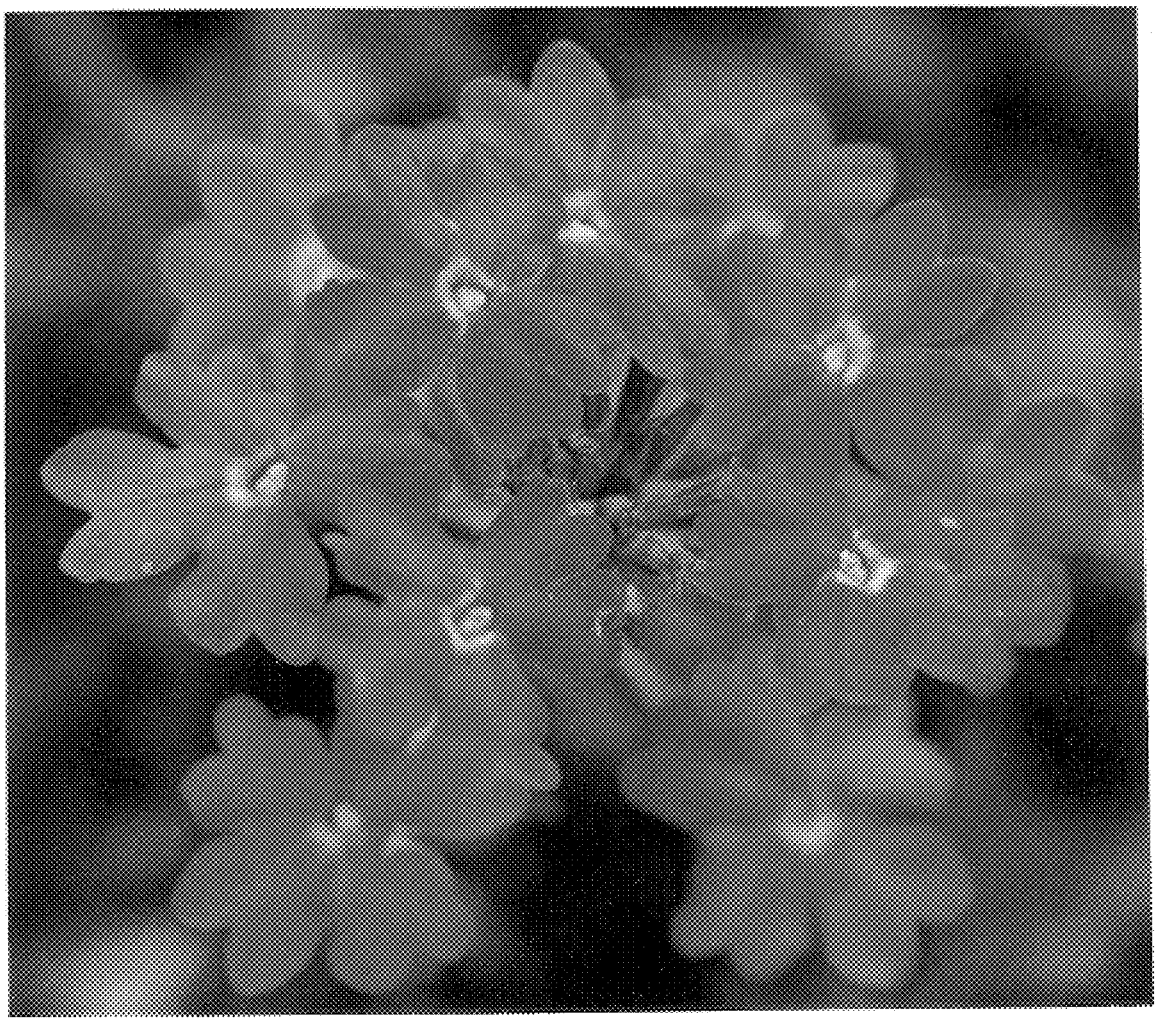
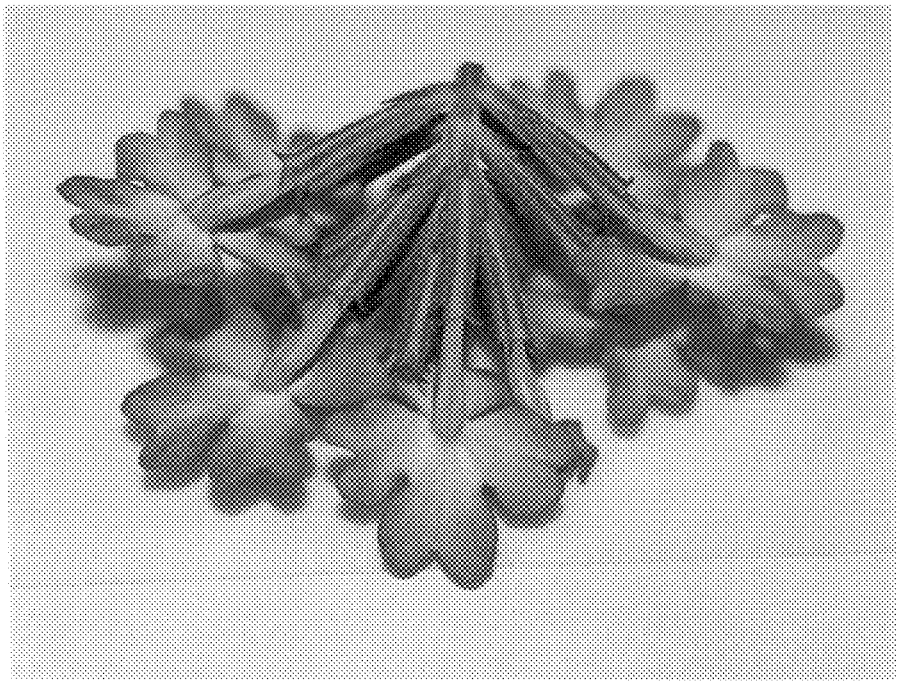

* * * * *